US008263711B2

(12) United States Patent
Krepski et al.

(10) Patent No.: US 8,263,711 B2
(45) Date of Patent: *Sep. 11, 2012

(54) (METH)ACRYLOYL-AZIRIDINE CROSSLINKING AGENTS AND ADHESIVE POLYMERS

(75) Inventors: Larry R. Krepski, White Bear Lake, MN (US); Peiwang Zhu, Woodbury, MN (US); Belma Erdogan-Haug, St. Paul, MN (US); Wen Jie Zhang, Shanghai (CN); Dang Xie, Shanghai (CN); Maureen A. Kavanagh, Stanchfield, MN (US); Marie Aloshyna ep Lesuffleur, Minneapolis, MN (US); Babu Gaddam, Woodbury, MN (US); Qing Wu, Shanghai (CN)

(73) Assignee: 3M Innovative Properties Company, St. Paul, MN (US)

( * ) Notice: Subject to any disclaimer, the term of this patent is extended or adjusted under 35 U.S.C. 154(b) by 154 days.

This patent is subject to a terminal disclaimer.

(21) Appl. No.: 12/849,878

(22) Filed: Aug. 4, 2010

(65) Prior Publication Data
US 2011/0152445 A1 Jun. 23, 2011

(30) Foreign Application Priority Data

Dec. 23, 2009 (CN) .......................... 2009 1 0261937

(51) Int. Cl.
*C08F 271/02* (2006.01)
(52) U.S. Cl. ........ 525/279; 525/242; 525/293; 525/298; 525/302; 525/308; 525/309; 525/329.7; 525/329.9; 525/330.3; 525/330.5; 525/374; 525/375; 525/383; 525/386; 156/325; 156/326; 156/327; 156/332; 524/86; 524/543; 524/556; 427/207.1; 427/208.4
(58) Field of Classification Search ................... 525/279, 525/242, 293, 298, 302, 308, 309, 329.7, 525/329.9, 330.3, 330.5, 374, 375, 383, 386; 156/325, 326, 327, 332; 524/86, 543, 556, 524/639; 427/207.1, 208.4
See application file for complete search history.

(56) References Cited

U.S. PATENT DOCUMENTS

| | | |
|---|---|---|
| RE24,906 E | 12/1960 | Ulrich |
| 3,243,429 A | 3/1966 | Ham |
| 3,337,533 A | 8/1967 | Ham |
| 3,511,897 A | 5/1970 | Endsley |
| 3,691,140 A | 9/1972 | Silver |
| 3,974,131 A * | 8/1976 | Puskas et al. ................. 526/263 |
| 4,026,880 A | 5/1977 | Mitchell |
| 4,062,886 A | 12/1977 | Turner |
| 4,166,152 A | 8/1979 | Baker et al. |
| 4,181,755 A | 1/1980 | Liu et al. |
| 4,225,665 A | 9/1980 | Schadt, III |
| 4,243,500 A | 1/1981 | Glennon |
| 4,303,485 A | 12/1981 | Levens |
| 4,304,705 A | 12/1981 | Heilmann et al. |
| 4,364,972 A | 12/1982 | Moon |
| 4,605,698 A | 8/1986 | Briden |
| 4,619,979 A | 10/1986 | Kotnour et al. |
| 4,636,432 A | 1/1987 | Shibano et al. |
| 4,656,218 A | 4/1987 | Kinoshita |
| 4,777,276 A | 10/1988 | Rasmussen et al. |
| 4,843,134 A | 6/1989 | Kotnour et al. |
| 5,045,569 A | 9/1991 | Delgado |
| 5,506,279 A | 4/1996 | Babu et al. |
| 5,532,112 A | 7/1996 | Kohler et al. |
| 5,534,391 A * | 7/1996 | Wang ........................ 430/271.1 |
| 5,741,543 A | 4/1998 | Winslow et al. |
| 5,753,768 A | 5/1998 | Ellis |
| 5,773,485 A | 6/1998 | Bennett et al. |
| 5,902,836 A | 5/1999 | Bennett et al. |
| 6,245,922 B1 | 6/2001 | Heilmann et al. |
| 6,294,249 B1 | 9/2001 | Hamer et al. |
| 6,521,682 B1 | 2/2003 | Costantino et al. |
| 6,734,256 B1 | 5/2004 | Everaerts et al. |
| 7,276,247 B2 | 10/2007 | Fansler et al. |
| 7,339,002 B2 | 3/2008 | Guo et al. |
| 7,385,020 B2 | 6/2008 | Anderson et al. |
| 7,393,901 B1 | 7/2008 | Filiatrault et al. |
| 7,459,489 B2 | 12/2008 | Lewandowski et al. |
| 7,612,122 B2 | 11/2009 | Herlihy et al. |
| 7,652,095 B2 | 1/2010 | Filiatrault et al. |
| 7,652,103 B2 | 1/2010 | Kavanagh et al. |
| 7,691,915 B2 | 4/2010 | Kim et al. |
| 7,714,076 B2 | 5/2010 | Krepski et al. |
| 2007/0213463 A1 | 9/2007 | Sherman et al. |
| 2007/0299211 A1 | 12/2007 | Chen et al. |
| 2009/0246390 A1 | 10/2009 | Krepski et al. |
| 2010/0081759 A1 | 4/2010 | Kavanagh et al. |
| 2010/0137469 A1 | 6/2010 | Zhu et al. |

FOREIGN PATENT DOCUMENTS

| | | |
|---|---|---|
| DE | 2630784 | 2/1977 |
| EP | 1 179 577 | 2/2002 |
| JP | 58-026869 | * 2/1983 |
| JP | 58026869 | 2/1983 |
| WO | WO 79/01013 | 11/1979 |
| WO | WO 95/10552 | 4/1995 |

(Continued)

OTHER PUBLICATIONS

ASTM D 3330/D 3330M-04, "Standard Test Method for Peel Adhesion of Pressure-Sensitive Tape", (2004), pp. 1-6, ASTM Int'l.
ASTM D 3654/D 3654M-06, "Standard Test Methods for Shear Adhesion of Pressure-Sensitive Tapes", (2006), pp. 1-6, ASTM Int'l.
Hubner et al., Makromolekulare Chem., vol. 11, No. 124, pp. 109-124, (1970).
Iwakura et al., "A Novel Preparation of Pseudoxzaolones," Tetraheron, vol. 23, pp. 3363-3373, Pergamon Press Ltd., (1967).
Kulkari et al., "Effect of Asymmetric Centers on Free Radical Polymerization and the Properties of Polymers: Methacrylyl Alanine, Methacrylyl Glutamic Acid, Acrylyl Glutamic Acid, and Their Polymers," Journal of Polymer Science, vol. 54, pp. 491-503, (1961).

(Continued)

*Primary Examiner* — Robert C Boyle
(74) *Attorney, Agent, or Firm* — Kent S. Kokko

(57) ABSTRACT

Described is a pre-adhesive, curable composition comprising an acid-functional (meth)acrylate copolymer and a novel (meth)acryloyl-aziridine crosslinking agent, which when crosslinked provides a pressure-sensitive adhesive composition.

15 Claims, No Drawings

FOREIGN PATENT DOCUMENTS

| WO | WO 97/05100 | | 2/1997 |
|---|---|---|---|
| WO | WO 02/38694 A1 | | 5/2002 |
| WO | WO 2004/029171 A1 | | 4/2004 |
| WO | WO 2005/092403 | | 10/2005 |
| WO | WO 2008/046000 | | 4/2008 |
| WO | WO 2008/100713 | | 8/2008 |
| WO | WO 2008/100755 | | 8/2008 |
| WO | 2009/006254 | | 1/2009 |
| WO | WO 2009-006254 | * | 1/2009 |
| WO | WO 2009/102623 | | 8/2009 |
| WO | WO 2009/120420 | | 10/2009 |

OTHER PUBLICATIONS

McCormick et al., "Water-Soluble Polymers," Encyclopedia of Polymer Science and Technology, vol. 12, pp. 452-521, Jul. 2004.

Pocius, "Adhesion and Adhesives Technology, An Introduction", (2002), $2^{nd}$ Edition, Hanser Gardner Publications, Inc., Cincinnati, OH.

PSTC-7, "Holding Power of Pressure Sensitive Tape", Revised (1989), pp. 37-39.

Rosenthal et al., "The Synthesis of β-Amino Mercaptans and β-Amino Thiosulfates via Ethylenimine Intermediates", Journal of Organic Chemistry, vol. 30, Issue 11, Nov. 1965, pp. 3689-3696.

Taylor et al., "The Synthesis of Vinyl Peptide Monomers," Journal of Polymer Science, Polymer Letters, vol. 7, pp. 597-603, (1969).

Partial International Search Report for PCT/US2010/060219, International Filing Date Dec. 14, 2010.

* cited by examiner

(METH)ACRYLOYL-AZIRIDINE CROSSLINKING AGENTS AND ADHESIVE POLYMERS

CROSS REFERENCE TO RELATED APPLICATIONS

This application claims priority from Chinese Application No. 200910261937.3, filed Dec. 23, 2009.

TECHNICAL FIELD OF THE INVENTION

This invention relates to pressure-sensitive adhesives and tape articles prepared therefrom. The tapes are characterized by exhibiting an overall balance of adhesive and cohesive characteristics and exceptional load bearing capabilities at elevated temperatures.

BACKGROUND OF THE INVENTION

Pressure-sensitive tapes are virtually ubiquitous in the home and workplace. In its simplest configuration, a pressure-sensitive tape comprises an adhesive and a backing, and the overall construction is tacky at the use temperature and adheres to a variety of substrates using only moderate pressure to form the bond. In this fashion, pressure-sensitive tapes constitute a complete, self-contained bonding system.

According to the Pressure-Sensitive Tape Council, pressure-sensitive adhesives (PSAs) are known to possess properties including the following: (1) aggressive and permanent tack, (2) adherence with no more than finger pressure, (3) sufficient ability to hold onto an adherend, and (4) sufficient cohesive strength to be removed cleanly from the adherend. Materials that have been found to function well as PSAs include polymers designed and formulated to exhibit the requisite viscoelastic properties resulting in a desired balance of tack, peel adhesion, and shear holding power. PSAs are characterized by being normally tacky at room temperature (e.g., 20° C.). PSAs do not embrace compositions merely because they are sticky or adhere to a surface.

These requirements are assessed generally by means of tests which are designed to individually measure tack, adhesion (peel strength), and cohesion (shear holding power), as noted in A.V. Pocius in Adhesion and Adhesives Technology: An Introduction, 2$^{nd}$ Ed., Hanser Gardner Publication, Cincinnati, Ohio, 2002. These measurements taken together constitute the balance of properties often used to characterize a PSA.

With broadened use of pressure-sensitive tapes over the years, performance requirements have become more demanding. Shear holding capability, for example, which originally was intended for applications supporting modest loads at room temperature, has now increased substantially for many applications in terms of operating temperature and load. So-called high performance pressure-sensitive tapes are those capable of supporting loads at elevated temperatures for 10,000 minutes. Increased shear holding capability has generally been accomplished by crosslinking the PSA, although considerable care must be exercised so that high levels of tack and adhesion are retained in order to retain the aforementioned balance of properties.

There are two major crosslinking mechanisms for acrylic adhesives: free-radical copolymerization of multifunctional ethylenically unsaturated groups with the other monomers, and covalent or ionic crosslinking through the functional monomers, such as acrylic acid. Another method is the use of UV crosslinkers, such as copolymerizable benzophenones or post-added photocrosslinkers, such as multifunctional benzophenones and triazines. In the past, a variety of different materials have been used as crosslinking agents, e.g., polyfunctional acrylates, acetophenones, benzophenones, and triazines. The foregoing crosslinking agents, however, possess certain drawbacks which include one or more of the following: high volatility; incompatibility with certain polymer systems; generation of corrosive or toxic by-products; generation of undesirable color; requirement of a separate photoactive compound to initiate the crosslinking reaction; and high sensitivity to oxygen.

SUMMARY

In one embodiment, the present disclosure provides a (meth)acryloyl-aziridine crosslinking agent of the formula:

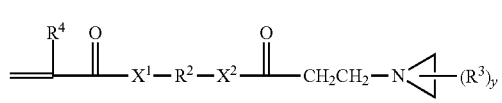

wherein
$X^1$ and $X^2$ are each independently —O— or —NH—;
$R^2$ is a (hetero)hydrocarbyl group,
$R^4$ is —H or $CH_3$;
y is 0 or 1;
each $R^3$ is independently —H or a $C_1$-$C_4$ alkyl group.

The present disclosure further provides a pre-adhesive, curable composition comprising an acid-functional (meth)acrylate copolymer and an (meth)acryloyl-aziridine crosslinking agent, which when crosslinked provides a pressure-sensitive adhesive composition. In one aspect, the disclosure provides a novel pre-adhesive syrup polymer composition comprising a) a first component acid-functional (meth)acrylate solute copolymer, b) a second component comprising at least one free-radically polymerizable solvent monomer, and c) an (meth)acryloyl-aziridine crosslinking agent. The pre-adhesive syrup polymer composition may be polymerized and crosslinked to produce a pressure-sensitive adhesive.

In another embodiment the disclosure provides an adhesive emulsion comprising an aqueous emulsion of the acid-functional (meth)acrylate copolymer, and the (meth)acryloyl-aziridine crosslinking agent which may be coated and crosslinked to form a pressure-sensitive adhesive. In a related embodiment, the present disclosure provides an adhesive emulsion comprising an aqueous emulsion of the reaction product of the acid-functional (meth)acrylate copolymer, and the (meth)acryloyl-aziridine crosslinking agent which may be coated and cured to form a pressure-sensitive adhesive.

For environmental reasons, there is a desire to move away from the use of volatile organic solvents (VOC's) in coating processes, and towards more environmentally friendly water-based materials, so the present invention provides a waterborne adhesive comprising an aqueous emulsion supra. Waterborne systems are desirable for cost, environmental, safety, and regulatory reasons. The aqueous system may be readily coated, and provides a pressure-sensitive adhesive when cured.

The pressure-sensitive adhesives, the crosslinked compositions, of this disclosure provide the desired balance of tack, peel adhesion, and shear holding power, and further conform to the Dahlquist criteria; i.e. the modulus of the adhesive at the application temperature, typically room temperature, is less than $3 \times 10^6$ dynes/cm at a frequency of 1 Hz.

The use of the (meth)acryloyl-aziridine crosslinking agent affords a number of advantages as compared to the use of conventional crosslinking agents for (meth)acrylic adhesives. These advantages include, but are not limited to, decreased sensitivity of the crosslinkable composition to oxygen; the avoidance of evolution of any toxic or corrosive by-products or discoloration of the final product; and the capability to be used as a post-curing crosslinking additive. Furthermore, the crosslinking agents have the following advantages over previously described agents: ease of synthesis, high solubility in the component monomers or organic solvents, and low cost starting materials.

In some embodiments, this disclosure provides an adhesive composition derived from renewable resources. In particular, the present invention provides an adhesive composition derived, in part, from plant materials. In some embodiments, the present invention further provides an adhesive article, wherein the substrate or backing is also derived from renewable resources. The increase in the price of oil, and concomitant petroleum-derived products, has led to volatile prices and supply for many adhesive products. It is desirable to replace all or part of the petroleum-based feedstocks with those derived from renewable sources, such as plants, as such materials become relatively cheaper, and are therefore both economically and socially beneficial. Therefore, the need for such plant-derived materials has become increasingly significant.

In this application "pre-adhesive" refers to the solution, suspension, or emulsion comprising an acid-functional (meth)acrylate copolymer, and an (meth)acryloyl-aziridine crosslinking agent which may be crosslinked to form a pressure-sensitive adhesive.

"Syrup polymer" refers to a solution of a solute polymer in one or more solvent monomers, the solution having a viscosity of from 500 to 10,000 cPs at 22° C. "Solution polymer" refers to a solution of a solute polymer in one or more organic solvents.

In this application, (meth)acrylic is inclusive of both methacrylic and acrylic.

As used herein, "alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent.

As used herein, the term "heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent.

As used herein, "aryl" is an aromatic group containing 6-18 ring atoms and can contain optional fused rings, which may be saturated, unsaturated, or aromatic. Examples of an aryl groups include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent.

As used herein, "(hetero)hydrocarbyl" is inclusive of hydrocarbyl alkyl and aryl groups, and heterohydrocarbyl heteroalkyl and heteroaryl groups, the later comprising one or more catenary oxygen heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

As used herein, "(meth)acryloyl is inclusive of methacryloyl and acryloyl.

DETAILED DESCRIPTION

The present disclosure provides a novel (meth)acryloyl-aziridine crosslinking agent of Formula I, and a pre-adhesive composition comprising an acid-functional (meth)acrylate copolymer and an (meth)acryloyl-aziridine crosslinking agent, which when crosslinked, provides a pressure-sensitive adhesive and pressure-sensitive adhesive articles.

The (meth)acrylate ester monomer useful in preparing the acid functional (meth)acrylate adhesive copolymer is a monomeric (meth)acrylic ester of a non-tertiary alcohol, which alcohol contains from 1 to 14 carbon atoms and preferably an average of from 4 to 12 carbon atoms.

Examples of monomers suitable for use as the (meth)acrylate ester monomer include the esters of either acrylic acid or methacrylic acid with non-tertiary alcohols such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctylalcohol, 2-ethyl-1-hexanol, 1-decanol, 2-propylheptanol, 1-dodecanol, 1-tridecanol, 1-tetradecanol, citronellol, dihydrocitronellol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomer are suitable. In some embodiments, the preferred (meth)acrylate ester monomer is the ester of (meth)acrylic acid with an alcohol derived from a renewable source, such as 2-octanol, citronellol, dihydrocitronellol.

In some embodiments it is desirable for the (meth)acrylic acid ester monomer to include a high $T_g$ monomer, have a $T_g$ of at least 25° C., and preferably at least 50° C. Suitable high Tg monomers include Examples of suitable monomers useful in the present invention include, but are not limited to, t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, and propyl methacrylate or combinations.

The (meth)acrylate ester monomer is present in an amount of 85 to 99.5 parts by weight based on 100 parts total monomer content used to prepare the polymer. Preferably (meth) acrylate ester monomer is present in an amount of 90 to 95 parts by weight based on 100 parts total monomer content. When high Tg monomers are included, the copolymer may include up to 30 parts by weight, preferably up to 20 parts by weight of the 85 to 99.5 parts by weight of (meth)acrylate ester monomer component. In such embodiments, the copolymer may comprise:

i. 55 to 69.5 parts by weight of an (meth)acrylic acid ester of non-tertiary alcohol;
  ii. 1 to 30 parts by weight of an (meth)acrylic acid ester having a $T_g$ of greater than 25° C.;
  iii. 0.5 to 15 parts by weight of an acid functional ethylenically unsaturated monomer;
  iv. 0 to 10 parts by weight of a non-acid functional, ethylenically unsaturated polar monomer;
  v. 0 to 5 parts vinyl monomer; and
  vi. 0 to 5 parts of a multifunctional (meth)acrylate; based on 100 parts by weight total monomer.

The polymer further comprises an acid functional monomer, where the acid functional group may be an acid per se, such as a carboxylic acid, or a portion may be salt thereof, such as an alkali metal carboxylate. Useful acid functional monomers include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

Due to their availability, acid functional monomers of the acid functional copolymer are generally selected from ethylenically unsaturated carboxylic acids, i.e. (meth)acrylic acids. When even stronger acids are desired, acidic monomers include the ethylenically unsaturated sulfonic acids and ethylenically unsaturated phosphonic acids. The acid functional monomer is generally used in amounts of 0.5 to 15 parts by weight, preferably 0.5 to 10 parts by weight, based on 100 parts by weight total monomer.

The polar monomers useful in preparing the copolymer are both somewhat oil soluble and water soluble, resulting in a distribution of the polar monomer between the aqueous and oil phases in an emulsion polymerization. As used herein the term "polar monomers" are exclusive of acid functional monomers.

Representative examples of suitable polar monomers include but are not limited to 2-hydroxyethyl (meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; poly(alkoxyalkyl) (meth)acrylates including 2-(2-ethoxyethoxy)ethyl (meth)acrylate, 2-ethoxyethyl (meth)acrylate, 2-methoxyethoxyethyl (meth)acrylate, 2-methoxyethyl methacrylate, polyethylene glycol mono(meth)acrylates; alkyl vinyl ethers, including vinyl methyl ether; and mixtures thereof. Preferred polar monomers include those selected from the group consisting of 2-hydroxyethyl (meth)acrylate and N-vinylpyrrolidinone. The polar monomer may be present in amounts of 0 to 10 parts by weight, preferably 0.5 to 5 parts by weight, based on 100 parts by weight total monomer.

When used, vinyl monomers useful in the (meth)acrylate polymer include vinyl esters (e.g., vinyl acetate and vinyl propionate), styrene, substituted styrene (e.g., α-methyl styrene), vinyl halide, and mixtures thereof. As used herein vinyl monomers are exclusive of acid functional monomers, acrylate ester monomers and polar monomers. Such vinyl monomers are generally used at 0 to 5 parts by weight, preferably 1 to 5 parts by weight, based on 100 parts by weight total monomer.

In order to increase cohesive strength of the coated adhesive composition, a multifunctional (meth)acrylate may be incorporated into the blend of polymerizable monomers. Multifunctional acrylates are particularly useful for emulsion or syrup polymerization. Examples of useful multifunctional (meth)acrylate include, but are not limited to, di(meth)acrylates, tri(meth)acrylates, and tetra(meth)acrylates, such as 1,6-hexanediol di(meth)acrylate, poly(ethylene glycol) di(meth)acrylates, polybutadiene di(meth)acrylate, polyurethane di(meth)acrylates, and propoxylated glycerin tri(meth) acrylate, and mixtures thereof. The amount and identity of multifunctional (meth)acrylate is tailored depending upon application of the adhesive composition. Typically, the multifunctional (meth)acrylate is present in amounts less than 5 parts based on total dry weight of adhesive composition. More specifically, the crosslinker may be present in amounts from 0.01 to 5 parts, preferably 0.05 to 1 parts, based on 100 parts total monomers of the adhesive composition.

The adhesive composition further comprises an (meth) acryloyl-aziridine crosslinking agent, in addition to the (meth)acrylate copolymer. The (meth)acryloyl-aziridine crosslinking agent is generally added in amounts of 0.005 to 5.0 parts by weight of an (meth)acryloyl-aziridine crosslinking agent, relative to 100 parts of the copolymer.

The (meth)acryloyl-aziridine crosslinking agent is of the general formula:

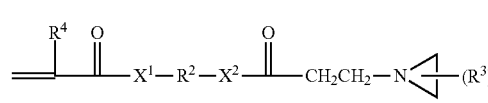

wherein
$X^1$ and $X^2$ are each independently —O— or —NH—;
$R^2$ is a (hetero)hydrocarbyl group,
$R^4$ is —H or $CH_3$;
y is 0 or 1;
each $R^3$ is independently —H or a $C_1$-$C_4$ alkyl group.

In some embodiments $R^2$ is a straight or branched chain alkylene preferably containing from one to about six carbon atoms. When $R^2$ is alkylene it can also contain hetero functional groups such as carbonyl, oxy, or catenary nitrogen, preferably fully substituted catenary nitrogen wherein the substituent is free of hydrogen-donor hydrogen bonding functional groups. In another embodiment $R^2$ can be arylene (e.g., 1,4-phenylene) or arylene substituted by lower alkyl or lower alkoxy $R^2$ can also be a combination of such arylene, alkenylene, and alkylene groups, such as 1,4-xylylene.

In one method, the (meth)acryloyl-aziridine crosslinking agent may be prepared by Michael addition of an aziridine compound to a (meth)acryloyl-acryloyl compound as shown in Scheme 1.

Scheme 1

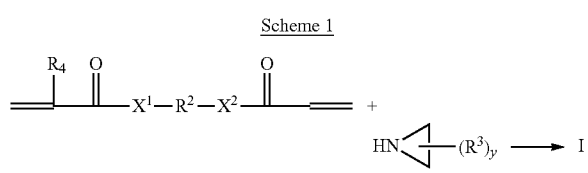

$X^1$ and $X^2$ are each independently —O— or —NH—;
$R^2$ is a (hetero)hydrocarbyl group,
each $R^3$ is independently —H or a $C_1$-$C_4$ alkyl group, and y is 0 or 1.

There is a differential reactivity between acryloyl and other ethylenically unsaturated polymerizable groups (such as methacryl, vinyl or allyl groups) with respect to Michael addition, which typically occurs easily between acryloyl groups and an aziridine compound; mild heating and the presence of a basic catalyst typically results in spontaneous Michael addition. The reaction may occur only with difficulty if at all, in the case of methacryl, allyl or vinyl groups.

For this reason, the reaction of Scheme 1 preferably has an acryloyl group (e.g., as part of acryloxy or acrylamido functionality), and additional ethylenically unsaturated groups such as (meth)acryloyl group (e.g., as part of methacrylate or methacrylamido functionality), vinyl groups or allyl groups. Most preferably the compound has an acryloyl groups and a methacryloyl group. Such groups that are relatively unreactive in Michael additions may be advantageously used to subsequently crosslink the adhesive copolymer by means of the photoinitiator. Advantageously, a composition may be prepared in which Michael addition occurs through the acryl groups to form a Michael adduct of Scheme 1, leaving photopolymerizable (meth)acryloyl groups unreacted. Such unreacted (meth)acryloyl groups may be subsequently photopolymerized.

As can be see in Scheme 1, the (meth)acryloyl-aziridine of formula I may be derived from an a (meth)acryloyl-acryloyl compound of the formula II in Scheme 2.

Scheme 2

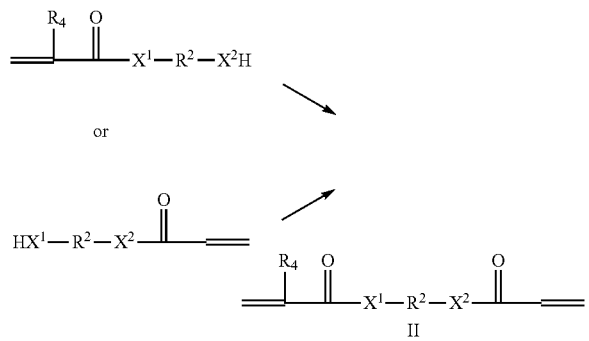

This in turn may be derived from precursor diol, diamine or hydroxylamine, followed by acrylation and methacrylation as in Scheme 2. In Scheme 2, the precursor compounds may also be reacted with an isocyanatoalkyl (meth)acryloyl compound.

Useful monoacrylates (for subsequent methacrylation) and monomethacrylate (for subsequent acrylation) include the mono (meth)acrylic acid ester of aliphatic diols such as ethyleneglycol, triethyleneglycol, 2,2-dimethyl-1,3-propanediol, 1,3-cyclopentanediol, 1-ethoxy-2,3-propanediol, 2-methyl-2,4-pentanediol, 1,4-cyclohexanediol, 1,6-hexamethylenediol, 1,2-cyclohexanediol, 1,6-cyclohexanedimethanol; the mono (meth)ylacrylic acid esters of aromatic diols such as resorcinol, pyrocatechol, bisphenol-A, and bis(2-hydroxyethyl) phthalate; the monoacrylic acid ester of aromatic triols such as pyrogallol, phloroglucinol, and 2-phenyl-2,2-methylolethanol. The monoacryloyl compounds may also be derived from the corresponding diamines.

In some embodiments, the (meth)acryloyl-aziridine of formula I may be derived the reaction between an azlactone compound and either of an aminoalkyl acryloyl compound or a hydroxyalkyl acryloyl compound as shown in Scheme 3:

Scheme 3

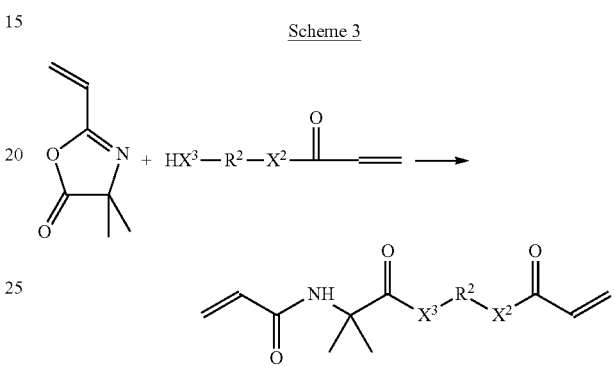

wherein $X^1$, $R^2$, $X^2$, x, $R^3$, and y are as previously defined for Formula I. With respect to Formula I, in such embodiments, —$X^1$—$R^2$— is —NH—C(CH$_3$)$_2$—CO—$X^3$—$R^2$—

The (meth)acryloyl-aziridine crosslinking agent may be copolymerized with the monomers of the acid functional (meth)acrylate copolymer, or may be added to the extant copolymer. It is believed that the aziridine group reacts with the pendent acid functional groups of the acid functional (meth)acrylate copolymer to form a carboxyethyleneamino linkage.

In one embodiment, where the (meth)acryloyl-aziridine is added to the extant polymer, the intermediate may be of the following structure, with the optional monomer units and unreacted (free) acid functional monomer units not shown. The pendent methacrylate group may be subsequently free radically polymerized to crosslink the copolymer. With respect to the $R^3$ group, it will be understood that it may be attached to the carbon adjacent to the —NH— group as depicted, or attached to the carbon adjacent the —O—, depending on the ring-opening.

formula:

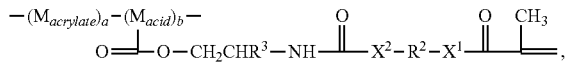

where $M_{acrylate}$ represents polymerized monomer units derived from (meth)acrylate monomers, $M_{acid}$ represents polymerized monomer units derived from acid functional monomers, and a and b are at least one.

and $R^1$, $X^1$, $R^2$, $X^2$, x, $R^3$, and y are as previously defined for Formula I.

It will be understood that a and b may be of values corresponding to the amounts of the monomers in the polymerizable composition, e.g. 85 to 99.5 parts by weight of an (meth) acrylic acid ester monomer; and 0.5 to 15 parts by weight of an acid functional monomer. Although not depicted in Formula II, other monomers may be present in the amounts previously recited.

In another embodiment, the (meth)acryloyl-aziridine is copolymerized with the other monomers to produce a copolymer having a pendent (meth)acryloyl-aziridine group as shown in Formula III.

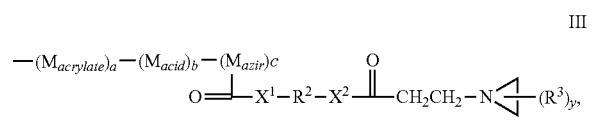

III

Where $M_{acrylate}$ represents polymerized monomer units derived from (meth)acrylate monomers, $M_{acid}$ represents polymerized monomer units derived from acid functional monomers, $M_{azir}$ represents polymerized monomer units derived from the aziridine crosslinking agent of claim 1; and a, b and c are at least one.

This pendent group may subsequently react with an acid group, resulting in ring-opening of the aziridine ring, and crosslinking of the copolymers as shown in Scheme 3.

where $M_{acrylate}$ represents polymerized monomer units derived from (meth)acrylate monomers, $M_{acid}$ represents polymerized monomer units derived from acid functional monomers, $M_{azir}$ represents polymerized monomer units derived from the (meth)acryloyl-aziridine of Formula I;

a, b and c are at least one;

and $R^1$, $X^1$, $R^2$, $X^2$, x, $R^3$, and y are as previously defined for Formula I. It will be understood that a, b and c may be of values corresponding to the amounts of the monomers in the polymerizable composition, i.e. 85 to 99.5 parts by weight of an (meth)acrylic acid ester monomer; 0.5 to 15 parts by weight of an acid functional monomer, and 0.005 to 5.0 parts by weight of the (meth)acryloyl-aziridine crosslinking agent. Although not depicted in Scheme 4, other monomers may be present in the amounts previously recited.

The acid functional copolymers can be prepared by any conventional free radical polymerization method, including solution, radiation, bulk, dispersion, emulsion, and suspension processes. The (meth)acrylate polymers may be prepared via suspension polymerizations as disclosed in U.S. Pat. No. 3,691,140 (Silver); 4,166,152 (Baker et al.); 4,636,432 (Shibano et al); 4,656,218 (Kinoshita); and 5,045,569 (Delgado). Each describes adhesive compositions, and the descriptions of polymerization processes are incorporated herein by reference.

Water-soluble and oil-soluble initiators useful in preparing the acid functional copolymers are initiators that, on exposure to heat, generate free-radicals which initiate (co)polymerization of the monomer mixture. Water-soluble initiators are preferred for preparing the (meth)acrylate polymers by emulsion polymerization. When used, initiators may comprise from about 0.05 to about 1 part by weight, preferably about 0.1 to about 0.5 part by weight based on 100 parts by weight of monomer components in the acid functional copolymers.

Suitable water-soluble initiators include but are not limited to those selected from the group consisting of potassium persulfate, ammonium persulfate, sodium persulfate, and mixtures thereof; oxidation-reduction initiators such as the reaction product of the above-mentioned persulfates and reducing agents such as those selected from the group consisting of sodium metabisulfite and sodium bisulfite; and 4,4'-azobis(4-cyanopentanoic acid) and its soluble salts (e.g., sodium, potassium). The preferred water-soluble initiator is potassium persulfate. Suitable oil-soluble initiators include Scheme 4

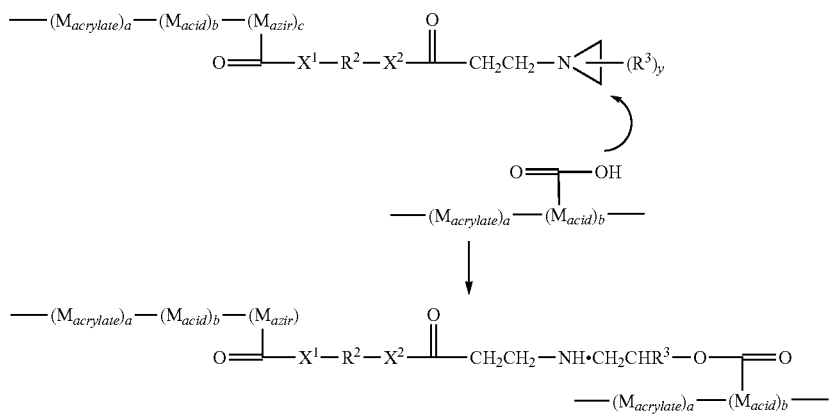

but are not limited to those selected from the group consisting of azo compounds such as VAZO™ 64 (2,2'-azobis(isobutyronitrile)), VAZO™ 67 (2,2'azobis (2-methylbutyronitrile)), and VAZO™ 52 (2,2'-azobis(2,4-dimethylpentanenitrile)), available from E.I. du Pont de Nemours Co., peroxides such as benzoyl peroxide and lauroyl peroxide, and mixtures thereof. The preferred oil-soluble thermal initiator is 2,2'-azobis-(2,4-dimethylpentanenitrile).

The copolymerizable emulsion mixture may optionally further comprise chain transfer agents to control the molecular weight of the resultant polymer. Examples of useful chain transfer agents include but are not limited to those selected from the group consisting of carbon tetrabromide, alcohols, mercaptans, and mixtures thereof. When present, the preferred chain transfer agents are isooctylthioglycolate and carbon tetrabromide. The emulsion mixture may further comprise up to about 0.5 parts by weight of a chain transfer agent, typically about 0.01 to about 0.5 parts by weight, if used, preferably about 0.05 parts by weight to about 0.2 parts by weight, based upon 100 parts by weight of the total monomer mixture.

Polymerization of the acid functional copolymers via emulsion techniques may require the presence of an emulsifier (which may also be called an emulsifying agent or a surfactant). Useful emulsifiers for the present invention include those selected from the group consisting of anionic surfactants, cationic surfactants, nonionic surfactants, and mixtures thereof.

Preferably, emulsion polymerization is carried out in the presence of anionic surfactant(s). A useful range of emulsifier concentration is from about 0.5 to about 8 weight percent, preferably from about 1 to about 5 weight percent, based on the total weight of all monomers of the emulsion pressure-sensitive adhesive.

The acid functional (meth)acrylate copolymers may be prepared by a batch, continuous or semi-continuous emulsion polymerization process. The polymerization generally comprises the steps of:
  (a) making a monomer premix comprising;
    (i) a (meth)acrylic acid ester monomer,
    (ii) an acid functional monomer;
    (iii) optionally a polar monomer,
    (iv) optionally a vinyl monomer,
    (v) optionally a multifunctional (meth)acrylate;
    (vi) optionally a chain transfer agent,
  (b) combining said premix with a water phase comprising:
    (i) water,
    (ii) a surfactant selected from the group consisting of anionic surfactants, nonionic surfactants, cationic surfactants, amphoteric surfactants, polymeric surfactants, and mixtures thereof,
    (iii) a free radical initiator, preferable a water soluble initiator,
  (c) concurrently agitating and heating said emulsion to a temperature of about 30° C. to about 80° C., and permitting polymerization of said monomers in the oil-in-water emulsion until a polymeric latex is formed. It will be understood that other mixtures may be used. For example, the acid functional monomer, or other hydrophilic monomers, may be added to the aqueous solution. In addition, once the emulsion mixture is prepared, the monomers may partition between the oil phase and the water phase, according to their respective partition coefficients. It will be understood that the monomer premix may also include the (meth)acryloyl-aziridine. Alternatively, the (meth)acryloyl-aziridine may be added to the extant polymer.

A neutralizing agent may be employed in the preparation of this copolymer. It may be employed at a level sufficient to neutralize all or a part of the acid groups of the polymer. Neutralization is achieved via the use of an alkali metal hydroxide or a combination of an alkali metal hydroxide with a minor amount of another neutralizing agent. A wide variety of other neutralizing agents may be used as will be understood by those skilled in the art. The selection of the other neutralizing agent, and the amount employed may be varied to achieve a desired result. However, the type and amount selected must not render the adhesive non-dispersible. Preferably ammonium, sodium and potassium hydroxide are used as neutralizing agents.

An alternate method of preparing acid functional (meth) acrylate copolymers comprises partially polymerizing monomers to produce a syrup polymer comprising the acid functional (meth)acrylate copolymer and unpolymerized monomers. The syrup polymer composition is polymerized to a useful coating viscosity, which may be coated onto a substrate (such as a tape backing) and further polymerized. Partial polymerization provides a coatable solution of the acid functional (meth)acrylate solute copolymer in one or more solvent monomers. Generally, the (meth)acryloyl-aziridine crosslinking agent is added to the partially polymerized composition, then coated on a suitable substrate and further polymerized. In an alternate embodiment, the (meth)acryloyl-aziridine crosslinking agent is added to the mixture of polymerizable monomers, and partially polymerized as previously described.

For syrup application processing, a preferred monomer mixture (second component) comprises 85 to 99.5 pbw of one or more (meth)acrylate ester monomers, 0.5 to 15 pbw of acid functional monomers, 0 to 10 pbw of one or more second, non-acid, polar monomers, and 0 to about 5 pbw of other vinyl monomers, based on 100 parts total monomer. It will be understood that the monomer mix may also include the (meth)acryloyl-aziridine. Alternatively, the (meth)acryloyl-aziridine may be added to the extant polymer.

The polymerizations may be conducted in the presence of, or preferably in the absence of, suitable solvents such as ethyl acetate, toluene and tetrahydrofuran which are unreactive with the functional groups of the components of the syrup polymer.

Polymerization can be accomplished by exposing the syrup polymer composition to energy in the presence of a photoinitiator. Energy activated initiators may be unnecessary where, for example, ionizing radiation is used to initiate polymerization. These photoinitiators can be employed in concentrations ranging from about 0.0001 to about 3.0 pbw, preferably from about 0.001 to about 1.0 pbw, and more preferably from about 0.005 to about 0.5 pbw, per 100 pbw of the solvent monomer(s).

A preferred method of preparation of the syrup polymer is photoinitiated free radical polymerization. Advantages of the photopolymerization method are that 1) heating the monomer solution is unnecessary and 2) photoinitiation is stopped completely when the activating light source is turned off. Polymerization to achieve a coatable viscosity may be conducted such that the conversion of monomers to polymer is up to about 30%. Polymerization can be terminated when the desired conversion and viscosity have been achieved by removing the light source and by bubbling air (oxygen) into the solution to quench propagating free radicals. The solute polymer(s) may be prepared conventionally in a non-monomeric solvent and advanced to high conversion (degree of polymerization). When solvent (monomeric or non-monomeric) is used, the solvent may be removed (for example by vacuum distillation) either before or after formation of the syrup polymer. While an acceptable method, this procedure involving a highly converted functional polymer is not preferred because an additional solvent removal step is required, another material may be required (the non-monomeric solvent), and dissolution of the high molecular weight, highly converted solute polymer in the monomer mixture may require a significant period of time.

Useful photoinitiators include benzoin ethers such as benzoin methyl ether and benzoin isopropyl ether; substituted acetophenones such as 2,2-dimethoxyacetophenone, available as Irgacure™ 651 photoinitiator (Ciba Specialty Chemicals), 2,2 dimethoxy-2-phenyl-1-phenylethanone, available as Esacure™ KB-1 photoinitiator (Sartomer Co.; West Chester, Pa.), and dimethoxyhydroxyacetophenone; substituted α-ketols such as 2-methyl-2-hydroxy propiophenone; aromatic sulfonyl chlorides such as 2-naphthalene-sulfonyl chloride; and photoactive oximes such as 1-phenyl-1,2-propanedione-2-(O-ethoxy-carbonyl)oxime. Particularly preferred among these are the substituted acetophenones.

Preferred photoinitiators are photoactive compounds that undergo a Norrish I cleavage to generate free radicals that can initiate by addition to the acrylic double bonds. The photoinitiator can be added to the mixture to be coated after the copolymer has been formed, i.e., photoinitiator can be added to the syrup polymer mixture. Such polymerizable photoinitiators are described, for example, in U.S. Pat. Nos. 5,902,836 and 5,506,279 (Babu et al.).

The syrup polymer composition and the photoinitiator may be irradiated with activating UV radiation to polymerize the monomer component(s). UV light sources can be of two types: 1) relatively low light intensity sources such as Blacklights which provide generally 10 mW/cm$^2$ or less (as measured in accordance with procedures approved by the United States National Institute of Standards and Technology as, for example, with a UVIMAP™ UM 365 L-S radiometer manufactured by Electronic Instrumentation & Technology, Inc., in Sterling, Va.) over a wavelength range of 280 to 400 nanometers and 2) relatively high light intensity sources such as medium pressure mercury lamps which provide intensities generally greater than 10 mW/cm$^2$, preferably between 15 and 450 mW/cm$^2$. Where actinic radiation is used to fully or partially polymerize the syrup polymer composition, high intensities and short exposure times are preferred. For example, an intensity of 600 mW/cm$^2$ and an exposure time of about 1 second may be used successfully. Intensities can range from about 0.1 to about 150 mW/cm$^2$, preferably from about 0.5 to about 100 mW/cm$^2$, and more preferably from about 0.5 to about 50 mW/cm$^2$. Such photoinitiators preferably are present in an amount of from 0.1 to 1.0 pbw per 100 pbw of the syrup polymer composition.

Accordingly, relatively thick coatings (e.g., at least about 1 mil or 25.4 micrometers) can be achieved when the extinction coefficient of the photoinitiator is low.

The degree of conversion can be monitored during the irradiation by measuring the index of refraction of the polymerizing medium as previously described. Useful coating viscosities are achieved with conversions (i.e. the percentage of available monomer polymerized) in the range of up to 30%, preferably 2-20%, more preferably from 5-15%, and most preferably from 7-12%. The molecular weight (weight average) of the solute polymer(s) is at least 100,000, preferably at least 500,000.

When preparing acid functional (meth)acrylate copolymers, it is expedient for the photoinitiated polymerization reactions to proceed to virtual completion, i.e., depletion of the monomeric components, at temperatures less than about 70° C. (preferably at 50° C. or less) with reaction times less than 24 hours, preferably less than 12 hours, and more preferably less than 6 hours. These temperature ranges and reaction rates obviate the need for free radical polymerization inhibitors, which are often added to acrylic systems to stabilize against undesired, premature polymerization and gelation. Furthermore, the addition of inhibitors adds extraneous material that will remain with the system and inhibit the desired polymerization of the syrup polymer and formation of the crosslinked pressure-sensitive adhesives. Free radical polymerization inhibitors are often required at processing temperatures of 70° C. and higher for reaction periods of more than about 6 to 10 hours.

In some embodiments, the acid functional (meth)acrylate copolymers may be prepared by solution methods. A typical solution polymerization method is carried out by adding the monomers, a suitable solvent, and an optional chain transfer agent to a reaction vessel, adding a free radical initiator, purging with nitrogen, and maintaining the reaction vessel at an elevated temperature, typically in the range of about 40 to 100° C. until the reaction is completed, typically in about 1 to 20 hours, depending upon the batch size and temperature. Examples of the solvent are methanol, tetrahydrofuran, ethanol, isopropanol, acetone, methyl ethyl ketone, methyl acetate, ethyl acetate, toluene, xylene, and an ethylene glycol alkyl ether. Those solvents can be used alone or as mixtures thereof. The monomer mixture may contain the (meth)acryloyl-aziridine crosslinking agent, or the crosslinking agent may be added to the extant polymer.

It is preferable to coat the adhesive composition soon after preparation. The adhesive polymer composition, (containing the copolymer, monomers and (meth)acryloyl-aziridine crosslinking agent), either as a syrup or solution are easily coated upon suitable substrates, such as flexible backing materials, by conventional coating techniques, then further polymerized, and cured or dried, to produce adhesive coated sheet materials. When emulsion polymerization techniques are used, an emulsion comprising the extant copolymer, (meth)acryloyl-aziridine crosslinking agent is coated and dried to produce adhesive coated sheet materials. The flexible backing material may be any material conventionally utilized as a tape backing, optical film or any other flexible material.

The pressure-sensitive adhesives may also contain one or more conventional additives. Preferred additives include tackifiers, plasticizers, dyes, antioxidants, and UV stabilizers. Such additives can be used if they do not affect the superior properties of the emulsion pressure-sensitive adhesives.

If tackifiers are used, then up to about 50% by weight, preferably less than 30% by weight, and more preferably less than 5% by weight based on the dry weight of the total adhesive polymer would be suitable. In some embodiments no tackifiers may be used. Suitable tackifiers for use with (meth)acrylate polymer dispersions include rosin acids, rosin esters, terpene phenolic resins, hydrocarbon resins, and cumarone indene resins. The type and amount of tackifier can affect properties such as contactability, bonding range, bond strength, heat resistance and specific adhesion.

Adhesive articles may be prepared by coating the adhesive or pre-adhesive composition of a suitable support, such as a flexible backing. Examples of materials that can be included in the flexible backing include polyolefins such as polyethylene, polypropylene (including isotactic polypropylene), polystyrene, polyester, polyvinyl alcohol, poly(ethylene terephthalate), poly(butylene terephthalate), poly(caprolactam), poly(vinylidene fluoride), polylactides, cellulose acetate, and ethyl cellulose and the like. Commercially available backing materials useful in the invention include kraft paper (available from Monadnock Paper, Inc.); cellophane (available from Flexel Corp.); spun-bond poly(ethylene) and poly(propylene), such as Tyvek™ and Typar™ (available from DuPont, Inc.); and porous films obtained from poly(ethylene) and poly(propylene), such as Teslin™ (available from PPG Industries, Inc.), and Cellguard™ (available from Hoechst-Celanese).

Backings may also be prepared of fabric such as woven fabric formed of threads of synthetic or natural materials such as cotton, nylon, rayon, glass, ceramic materials, and the like or nonwoven fabric such as air laid webs of natural or synthetic fibers or blends of these. The backing may also be formed of metal, metallized polymer films, or ceramic sheet materials may take the form of any article conventionally known to be utilized with pressure-sensitive adhesive compositions such as labels, tapes, signs, covers, marking indicia, and the like.

The above-described compositions are coated on a substrate using conventional coating techniques modified as appropriate to the particular substrate. For example, these compositions can be applied to a variety of solid substrates by methods such as roller coating, flow coating, dip coating, spin coating, spray coating knife coating, and die coating. These various methods of coating allow the compositions to be placed on the substrate at variable thicknesses thus allowing a wider range of use of the compositions. Coating thicknesses may vary as previously described. The solutions may be of any desirable concentration, and degree of conversion, for subsequent coating, but is typically between 20 to 70 wt. % polymer solids, and more typically between 30 and 50 wt. % solids, in solvent. The emulsions also may be of any desirable concentration for subsequent coating, but is typically between 30 to 70 wt. % polymer solids, and generally contains less than 2% unreacted monomer. The syrup polymers may be of any desirable concentration for subsequent coating, but is typically between 5 to 20 wt. % polymer solids in monomer. The desired concentration may be achieved by further dilution of the coating composition, or by partial drying.

The flexible support may also comprise a release-coated substrate. Such substrates are typically employed when an adhesive transfer tape is provided. Examples of release-coated substrates are well known in the art and include, by way of example, silicone-coated kraft paper and the like. Tapes of the invention may also incorporate a low adhesion backsize (LAB) which are known in the art.

EXAMPLES

Objects and advantages of this invention are further illustrated by the following examples. The particular materials and amounts, as well as other conditions and details, recited in these examples should not be used to unduly limit this invention.

Test Methods

Peel Adhesion Test [ASTM D 3330/D 3330M-04]

Two 0.5 inch strips of adhesive coated onto Mitsubishi Hostphan™ primed polyester film were adhered to a glass plate by rolling a 2 kg roller onto the tape. The force required to peel the tape at an angle of 180 degrees was measured in ounces per 0.5 inches with a platen speed of 90 inches per minute and 12 inches per minute. The measurements for the two tape samples were averaged.

Shear Strength Test [ASTM D-3654/D 3654M 06, PSTC-7]

High Temperature Shears: A 0.5 inch strip of adhesive coated onto Mitsubishi Hostaphan™ primed polyester film was adhered by its adhesive to a stainless steel (SS) substrate and cut down to leave a 1 in by 0.5 inch sample for 70° C. temperature shear testing. A weight of 2 kg was rolled over the adhered portion. A 500 g load was attached to the tape sample for testing. Each sample was suspended until failure and/or test terminated. The time to failure as well as the mode of failure was recorded. Samples were run in triplicate and averaged for the tables below.

Room Temperature Shears: A 0.5 inch strip of adhesive coated onto Mitsubishi Hostphan™ primed polyester film was adhered by its adhesive to a stainless steel (SS) substrate and cut down to leave a 0.5 in by 0.5 inch sample for room temperature shear testing. A weight of 2 kg was rolled over the adhered portion. A 1000 g load was attached to the tape sample for testing. Each sample was suspended until failure and/or test terminated. The time to failure as well as the mode of failure was recorded. Samples were run in triplicate and averaged for the tables below.

Materials

| Abbreviation or Trade Designation | Description |
|---|---|
| IOA | Isooctyl Acrylate |
| AA | Acrylic Acid |
| IBOA | Isobornyl Acrylate |
| HDDA | 1,6-Hexanediol diacrylate |
| Irgacure 651 | 2,2-dimethoxy-2-phenylacetophenone from CIBA Corporation Tarrytown, NY |
| Regalrez 6108 | Hydrocarbon resin used as tackifier available from Eastman Chemical Company, Kingsport, TN |

Preparation of (Meth)Acryloyl-Aziridine Crosslinking Agents

TABLE 1

(Meth)acryloyl-Aziridine Crosslinking Agents

| ID Number | Structure | Mol. Wt. (g/mol) |
|---|---|---|
| I | 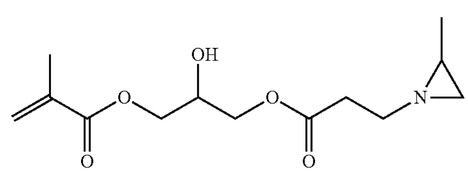 | 271.31 |

TABLE 1-continued (Meth)acryloyl-Aziridine Crosslinking Agents

| ID Number | Structure | Mol. Wt. (g/mol) |
|---|---|---|
| II | 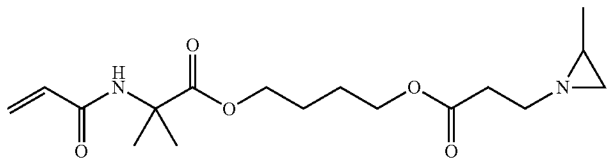 | 340.41 |
| III | 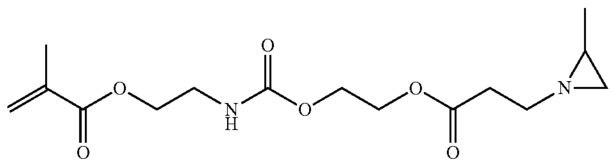 | 328.36 |

Preparation of Compound I: 2-methylacrylic acid 2-hydroxy-3-[3-(2-methylaziridin-1-yl)propionyloxy]propyl estr To a 250 mL round bottomed flask were added 3-(acryloyloxy)-2-hydroxypropyl methacrylate (32.1 g, 0.15 mol, available from Aldrich) and 2-methylaziridine (10.8 g, about 0.17 mol, 90% pure, available from Aldrich) to cause a slight exotherm. The reaction mixture was allowed to stand at room temperature overnight. Excess 2-methylaziridine was removed at reduced pressure to leave the desired product (40.4 g) as a colorless liquid. NMR and IR spectral analyses confirmed the structure of the product.

Preparation of Compound II: 4-{[3-(2-methylaziridin-1-yl)propanoyl]oxy}butyl N-acryloyl-2-methylalaninate Step 1: Preparation of 4-(acryloyloxy)butyl N-acryloyl-2-methylalaninate

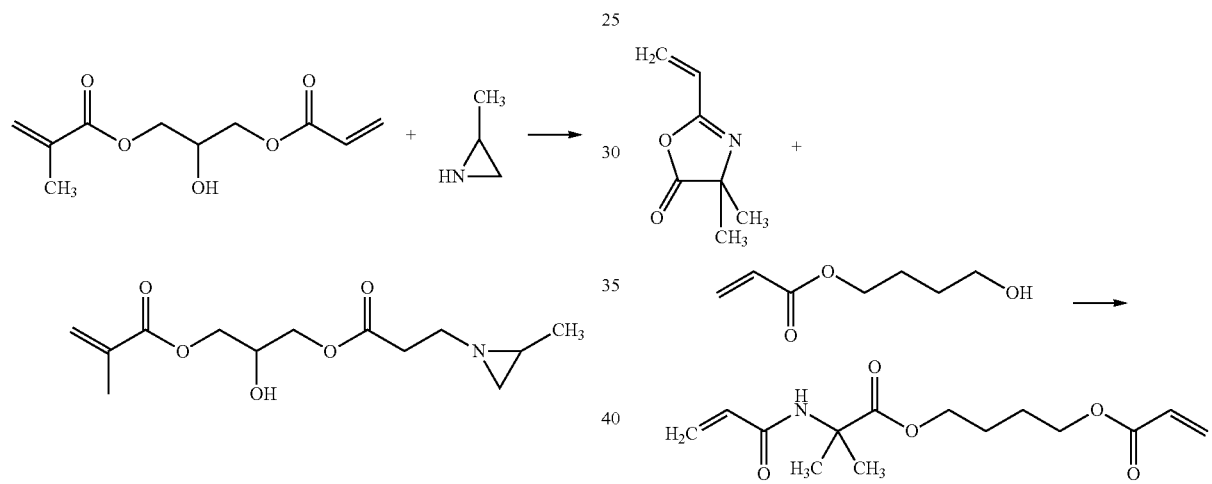

Step 1

Vinyldimethyl azlactone (13.9 g, 0.10 mol, available from 3M), 4-hydroxybutyl acrylate (14.4 g, 0.10 mol, available from TCI America) and 3 drops of 1,8-diazabicyclo[5.4.0]undec-7-ene (available from Aldrich) were mixed in a 4 ounce jar. The jar was sealed and placed in a 70° C. oven for 4 days. After cooling to room temperature, IR and NMR analyses confirmed that the desired product had been formed.

Step 2: Preparation of 4-{[3-(2-methylaziridin-1-yl)propanoyl]oxy}butyl N-acryloyl-2-methylalaninate

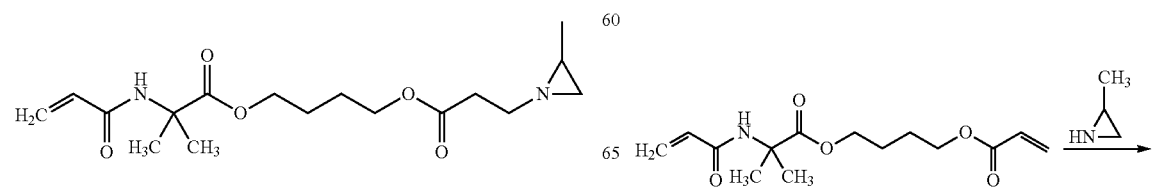

-continued

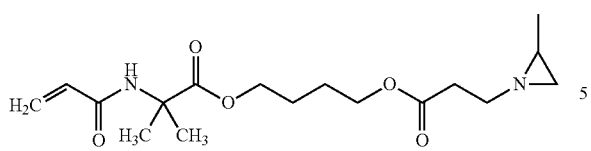

The product of Step 1 (4-(acryloyloxy)butyl N-acryloyl-2-methylalaninate, 10.0 g, 35 mmol) was mixed with 2-methylaziridine (2.7 g, about 42 mmol, 90% pure, available from Aldrich) to cause a slight exotherm. The reaction mixture was allowed to stand at room temperature overnight. Excess 2-methylaziridine was removed at reduced pressure to leave the desired product (11.8 g) as a colorless liquid. NMR and IR spectral analyses confirmed the structure of the product.

Preparation of Compound III: 2-{[(2-{[3-(2-methylaziridin-1-yl)propanoyl]oxy}ethoxy) carbonyl]amino}ethyl 2-methylacrylate

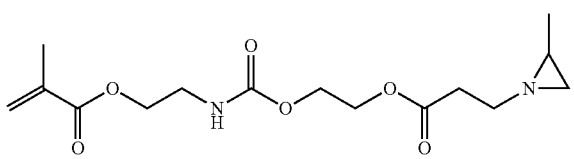

Step 1: 2-({[2-(acryloyloxy)ethoxy]carbonyl}amino)ethyl 2-methylacrylate

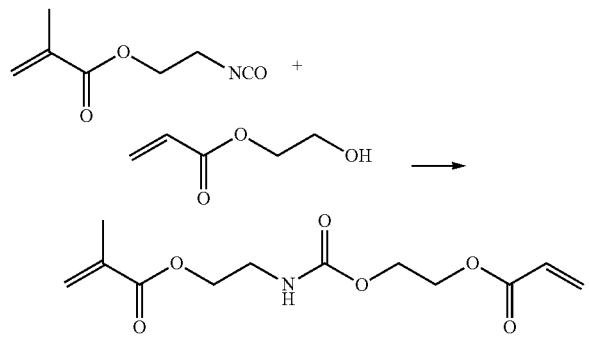

In a 4 ounce glass jar were mixed 2-isocyanatoethyl methacrylate (15.5 g, 0.10 mol, available from Aldrich), 2-hydroxyethyl acrylate (11.6 g, 0.10 mol, available from Aldrich), and one drop of di-n-butyltin dilaurate (available from Alfa Aesar) to cause a slight exotherm. The jar was cooled briefly in an ice bath, and then left at room temperature overnight. NMR and IR spectral analyses confirmed the structure of the product.

Step 2: Preparation of 2-{[(2-{[3-(2-methylaziridin-1-yl)propanoyl]oxy}ethoxy)carbonyl]amino}ethyl 2-methylacrylate

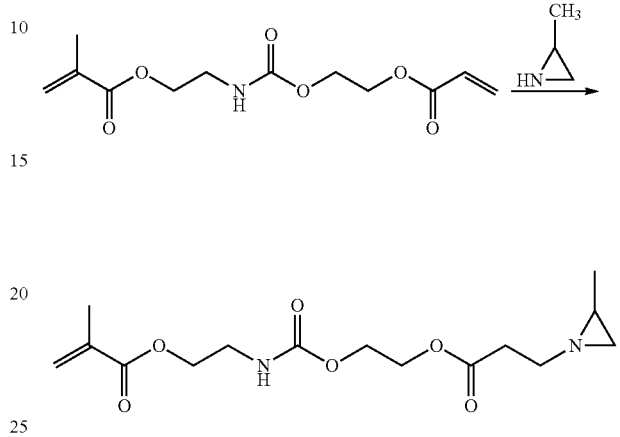

The product of Step 1 (2-({[2-(acryloyloxy)ethoxy] carbonyl}amino)ethyl 2-methylacrylate, 10.0 g, 37 mmol) was mixed with 2-methylaziridine (2.8 g, about 44 mmol, 90% pure, available from Aldrich) to cause a slight exotherm. The reaction mixture was allowed to stand at room temperature overnight. Excess 2-methylaziridine was removed at reduced pressure to leave the desired product (12.0 g) as a colorless liquid. NMR and IR spectral analyses confirmed the structure of the product.

Examples 2A-H and Comparative C1 and C2

Preparation of the Syrup Copolymer

A one quart jar was charged with 450 g of isooctyl acrylate (IOA, 90 parts), 50 g of acrylic acid (AA, 10 parts), and 0.20 g of 2,2-dimethoxy-2-phenylacetophenone photoinitiator (Irgacure™ 651, Ciba Specialty Chemicals Inc, 0.04 phr). The monomer mixture was purged with nitrogen for 20 minutes then exposed to low intensity ultraviolet radiation until a coatable syrup copolymer was prepared, after which an additional 0.8 g (0.16 phr) of the photoinitiator was added.

The pre-adhesive polymer syrup was blended with various concentrations of the (Meth)acryloyl-Aziridine crosslinking agent as shown in Table 1. The formulations were then coated on Mitsubishi Hostaphan™ primed polyester film at a 2 mil (~50 micrometers) thickness for the syrup pre-adhesive formulations and cured at 500 mJ/cm². The peel and shear data are shown in Table 2.

For comparative purposes, control examples using no crosslinking agent (Example C1), or using 1,6-hexanedioldiacrylate (using 0.08 phr in Example C2) as the crosslinking agent were also prepared and tested. Peel Adhesion and Shear Strength were measured for tapes prepared from these adhesives as described in the test methods above.

TABLE 2

Syrup Copolymer IOA/AA (90/10)

| ID | HDDA | (Meth)acryloyl-Aziridine Crosslinker | | | Shear | | 180° Peel (OZ/inch) | |
|----|------|---|---|---|---|---|---|---|
| | | I | II | III | RT | 70° C. | (90"/min) | (12"/min) |
| C1 | 0 | 0 | 0 | 0 | 662 (co) | 195 (co) | 77.2 | 69.9 |
| C2 | 0.08 | 0 | 0 | 0 | 10 k+ | 10 k+ | 75.5 | 66.2 |
| 2A | 0 | 0.05 | 0 | 0 | 10 k+ | 10 k+ | 76.5 | 71.2 |
| 2B | 0 | 0.1 | 0 | 0 | 10 k+ | 10 k+ | 76.9 | 68.3 |
| 2C | 0.08 | 0.05 | 0 | 0 | 10 k+ | 10 k+ | 78.0 | 70.3 |
| 2D | 0.08 | 0.1 | 0 | 0 | 10 k+ | 10 k+ | 79.9 | 70.4 |
| 2E | 0 | 0 | 0.05 | 0 | 10 k+ | 10 k+ | 80.5 | 71.5 |
| 2F | 0 | 0 | 0.1 | 0 | 10 k+ | 10 k+ | 82.2 | 72.5 |
| 2G | 0 | 0 | 0 | 0.05 | 10 k+ | 10 k+ | 77.8 | 71.5 |
| 2H | 0 | 0 | 0 | 0.1 | 10 k+ | 10 k+ | 78.7 | 68.7 |

Examples 3A-L and Comparative C3 and C4

Preparation of the Syrup Copolymer

A one quart jar was charged with 400 g of isooctyl acrylate (IOA, 80 parts), 95 g of isobornyl acrylate (IBOA, 19 parts), 5 g of acrylic acid (AA, 1 parts), and 0.20 g of 2,2-dimethoxy-2-phenylacetophenone photoinitiator (Irgacure™ 651, Ciba Specialty Chemicals Inc, 0.04 phr). The monomer mixture was purged with nitrogen for 20 minutes then exposed to low intensity ultraviolet radiation until a coatable syrup copolymer was prepared, after which an additional 0.80 g (0.16 phr) of the photoinitiator was added.

The pre-adhesive polymer syrup was blended with various concentrations of the (Meth)acryloyl-Aziridine crosslinking agent as shown in Table 1. The formulations were then coated on Mitsubishi Hostaphan™ primed polyester film at a 2 mil (~50 micrometers) thickness for the syrup preadhesive formulations and cured at 560 mJ/cm². The peel and shear data are shown in Table 3.

For comparative purposes, control examples using no crosslinking agent (Example C3), or using 1,6-hexanedioldiacrylate (using 0.08 phr in Example C4) as the crosslinking agent were also prepared and tested. Peel Adhesion and Shear Strength were measured for tapes prepared from these adhesives as described in the test methods above.

What is claimed is:

1. A crosslinkable composition comprising an acid-functional (meth)acrylate copolymer and the (meth)acryloyl-aziridine crosslinking agent of the formula:

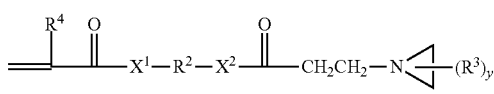

wherein
$X^1$ and $X^2$ are each independently —O— or —NH—;
$R^2$ is a (hetero)hydrocarbyl group,
$R^4$ is —H or $CH_3$;
y is 0 or 1;
each $R^3$ is independently —H or a $C_1$-$C_4$ alkyl group.

2. The crosslinkable composition of claim 1 wherein $R^2$ is —$CH_2$—$CH(OH)CH_2$—.

3. The crosslinkable composition of claim 1 wherein $R^2$ is an alkylene group.

4. The crosslinkable composition of claim 1 wherein $R^2$ is a poly(alkyleneoxy) group.

5. The crosslinkable composition of claim 1 wherein the acid-functional (meth)acrylate copolymer comprises:

TABLE 3

Syrup Copolymer IOA/IBOA/AA (80/19/1)

| ID | HDDA | Regalrez 6108 | (Meth)acryloyl-Aziridine Crosslinker | | | Shear (min) | | 180° Peel (OZ/inch) | |
|----|------|------|---|---|---|---|---|---|---|
| | | | I | II | III | RT | 70° C. | (90"/min) | (12"/min) |
| C3 | 0 | 0 | 0 | 0 | 0 | 1 (co) | 1 (co) | 83.1 | 56.7 |
| C4 | 0.08 | 0 | 0 | 0 | 0 | 119 | 10 k+ | 71.7 | 39.5 |
| 3A | 0 | 0 | 0.1 | 0 | 0 | NT | 10 k+ | 59.1 | 29.8 |
| 3B | 0.08 | 0 | 0.05 | 0 | 0 | NT | 10 k+ | 57.4 | 29.0 |
| 3C | 0.08 | 0 | 0.1 | 0 | 0 | NT | 10 k+ | 51.1 | 22.0 |
| 3D | 0 | 15 | 0.1 | 0 | 0 | NT | 10 k+ | 91.1 | 54.9 |
| 3E | 0 | 0 | 0 | 0.05 | 0 | 395 | 10 k+ | 79.1 | 46.0 |
| 3F | 0 | 0 | 0 | 0.1 | 0 | 406 | 10 k+ | 73.3 | 40.8 |
| 3G | 0 | 15 | 0 | 0.05 | 0 | 526 | 10 k+ | 116.5 | 76.8 |
| 3H | 0 | 15 | 0 | 0.1 | 0 | 551 | 10 k+ | 105.2 | 67.8 |
| 3I | 0 | 0 | 0 | 0 | 0.05 | 65 | 1219 | 80.1 | 47.7 |
| 3J | 0 | 0 | 0 | 0 | 0.1 | 407 | 10 k+ | 76.0 | 44.2 |
| 3K | 0 | 15 | 0 | 0 | 0.05 | 69 | 58 | 113.3 | 71.5 |
| 3L | 0 | 15 | 0 | 0 | 0.1 | 776 | 10 k+ | 105.9 | 70.4 | i. 85 to 99.5 parts by weight of an (meth)acrylic acid ester of non-tertiary alcohol;
ii. 0.5 to 15 parts by weight of an acid functional ethylenically unsaturated monomer;
iii. 0 to 10 parts by weight of a non-acid functional, ethylenically unsaturated polar monomer;
iv. 0 to 5 parts vinyl monomer; and
v. 0 to 5 parts of a multifunctional (meth)acrylate;
based on 100 parts by weight total monomer.

6. The crosslinkable composition of claim 1 comprising 0.005 to 5.0 parts by weight of an (meth)acryloyl-aziridine crosslinking agent, relative to 100 parts of the copolymer.

7. The crosslinkable composition of claim 5 wherein said copolymer comprises 0.5 to 5 parts by weight of acrylic acid and 1 to 5 parts by weight of a non-acid functional, ethylenically unsaturated monomer.

8. The crosslinkable composition of claim 5 comprising 1 to 5 parts of a vinyl monomer selected from vinyl esters, styrene, substituted styrene, vinyl halide, vinyl propionate, and mixtures thereof.

9. The crosslinkable composition of claim 5 wherein said non-tertiary alcohol of said (meth)acrylic acid ester of non-tertiary alcohol is selected from 2-octanol or dihydrocitronellol.

10. The crosslinkable composition of claim 1 comprising a syrup polymer composition comprising:
a) first component solute copolymer comprising:
i. 85 to 99.5 parts by weight of an (meth)acrylic acid ester of non-tertiary alcohol;
ii. 0.5 to 15 parts by weight of an acid functional monomer;
iii. 0 to 10 parts by weight of a non-acid functional, ethylenically unsaturated polar monomer;
iv. 0 to 5 parts vinyl monomer, and
b) a second component comprising at least one free-radically polymerizable solvent monomer, and
c) 0.005 to 5.0 parts by weight of the (meth)acryloyl-aziridine crosslinking agent.

11. A polymer derived from the crosslinkable composition of claim 1 of the formula:

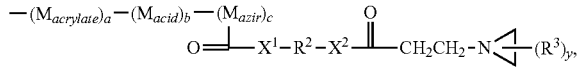

where
$M_{acrylate}$ represents polymerized monomer units derived from (meth)acrylate monomers,
$M_{acid}$ represents polymerized monomer units derived from acid functional monomers,
$M_{azir}$ represents polymerized monomer units derived from the aziridine crosslinking agent of claim 1; and
a, b and c are at least one.

12. A crosslinked polymer derived from crosslinking of the polymer of claim 11.

13. A polymer derived from the crosslinkable composition of claim 1 of the formula:

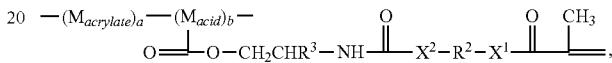

$M_{acrylate}$ represents polymerized monomer units derived from (meth)acrylate monomers,
$M_{acid}$ represents polymerized monomer units derived from acid functional monomers, and
a and b are at least one.

14. A crosslinked polymer derived from free-radically crosslinking of the polymer of claim 13.

15. A crosslinkable composition comprising an emulsion comprising:
(a) 30 to about 70 weight percent, based on the total weight of the emulsion, of the crosslinkable composition of claims 1, and
(b) 30 to 70 weight percent of an aqueous phase comprising a surfactant, based on the total weight of the emulsion.

* * * * *

UNITED STATES PATENT AND TRADEMARK OFFICE
CERTIFICATE OF CORRECTION

PATENT NO. : 8,263,711 B2  Page 1 of 1
APPLICATION NO. : 12/849878
DATED : September 11, 2012
INVENTOR(S) : Larry R Krepski It is certified that error appears in the above-identified patent and that said Letters Patent is hereby corrected as shown below:

Column 20
Line 58, delete "(-50" and insert -- (~50 --, therefor.

Column 24
Line 23, in Claim 13, before "$M_{acrylate}$" insert -- where --.
Line 35, in Claim 15, delete "claims 1," and insert -- claim 1, --, therefor.

Signed and Sealed this
Twenty-ninth Day of January, 2013

David J. Kappos
*Director of the United States Patent and Trademark Office*